(12) United States Patent
Yanagisawa et al.

(10) Patent No.: US 6,706,284 B2
(45) Date of Patent: Mar. 16, 2004

(54) BITTERNESS-REDUCED ORAL PHARMACEUTICAL COMPOSITION

(75) Inventors: Masahiro Yanagisawa, Itabashi-ku (JP); Takao Mizumoto, Tsukuba (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/096,906

(22) Filed: Mar. 14, 2002

(65) Prior Publication Data

US 2003/0017222 A1 Jan. 23, 2003

(30) Foreign Application Priority Data

Mar. 15, 2001 (JP) .................................. P. 2001-074190

(51) Int. Cl.$^7$ ................................. A61K 9/28
(52) U.S. Cl. ................. 424/474; 424/464; 424/477; 424/478; 424/482; 424/440; 424/451; 424/456; 424/457; 424/458; 424/460; 424/461; 424/463; 424/468; 424/469; 424/470; 424/475; 424/479; 424/480; 424/481
(58) Field of Search ................. 424/435, 464, 424/477, 478, 482, 440, 451, 456, 457, 458, 460, 461, 463, 468, 469, 470, 474, 475, 479, 480, 481

(56) References Cited

U.S. PATENT DOCUMENTS

| 4,572,832 A | * | 2/1986 | Kigasawa et al. |
| 5,576,014 A | | 11/1996 | Mizumoto et al. |
| 5,672,364 A | | 9/1997 | Kato et al. |
| 5,720,974 A | | 2/1998 | Makino et al. |
| 6,103,269 A | * | 8/2000 | Wunderlich et al. |

FOREIGN PATENT DOCUMENTS

| JP | 9-48726 A | 2/1997 |
| JP | 2919771 B2 | 4/1999 |
| JP | 2000-327561 A | 11/2000 |

* cited by examiner

*Primary Examiner*—Francisco Prats
*Assistant Examiner*—Susan D. Coe
(74) *Attorney, Agent, or Firm*—Sughrue Mion, PLLC

(57) ABSTRACT

The invention relates to an oral pharmaceutical composition which has excellent drug release-controlling ability in the mouth even 5 to 10 minutes after its administration and also has excellent drug releasing ability in the digestive tract without using capsules. It also relates to an oral pharmaceutical composition which comprises one or more drugs having a bitter taste, one or more solid proteins, and one or more pharmaceutically acceptable polymer bases, wherein the proteins are present in the polymer bases preferably as particles.

19 Claims, No Drawings

BITTERNESS-REDUCED ORAL PHARMACEUTICAL COMPOSITION

FIELD OF THE INVENTION

This invention relates to an oral pharmaceutical composition in which bitterness of a drug having a bitter taste is reduced. Particularly, it relates to a bitterness-reduced oral pharmaceutical composition, which comprises one or more drugs having a bitter taste, one or more solid proteins and one or more pharmaceutically acceptable water-insoluble polymer bases, wherein the proteins are present in the polymer bases particularly as particles.

BACKGROUND OF THE INVENTION

Intrabuccally quick disintegrating tablets can be easily taken even by patients having a difficulty in swallowing. Since a drug having strong bitterness has a low bitterness-feeling concentration, so-called a threshold value, one feels bitterness when the drug is remained in a trace amount in the mouth. Accordingly, when a drug having strong bitterness is applied to intrabuccally quick disintegrating tablets, they cannot be taken easily because the period of time to feel bitterness in the mouth becomes apparently longer than the case of drugs having less bitterness. In addition, intrabuccally quick disintegrating tablets are regarded in most cases as a dosage form in which the taking ability of conventional tablets already on the market is improved. Thus, insurance of bioavailability after made into intrabuccally quick disintegrating tablets is an item naturally required to guarantee their quality. Virtually nothing is known about bitterness-reducing techniques for solving these problems by simultaneously achieving conflicting items, namely the control of excellent drug release in the mouth and the insurance of excellent drug release in the digestive tract, and further enabling application to intrabuccally quick disintegrating tablets.

It is well known that capsules are prepared by filling gelatin capsules with, e.g., a bitter drug and a filler as a preparation technique for masking bitterness of the bitter drug. However, since capsules are regarded as a dosage form which cannot be taken easily by patients having weak swallowing ability, particularly by old persons and babies, and when the current situation for the improvement of compliance is taken into consideration, selection of a bitterness controlling technique by capsules cannot always be said effective. Concern has been directed toward the development of a technique for controlling bitterness by a preparation designing of a drug itself or a preparation designing of a form containing the drug.

The current method frequently and generally used as a technique for controlling bitterness by a preparation designing is a method to coat granules or powders containing a bitter drug or a bitter drug itself making use of a pH-independent water-insoluble polymer base such as ethyl cellulose. In this method, it is intended to control release of a drug in the mouth to a minimum drug concentration human can feel its bitterness, namely threshold value or less, so that a drug having lower threshold value (a drug having stronger bitterness) requires larger coating amount to control releasing amount of the drug at a lower level. Thus, in the general coating method which uses a pH-independent water-insoluble polymer base, when taste of a bitter drug, particularly a bitter drug having low threshold value, in the mouth is controlled, namely when the drug release at an early stage is controlled, or when the controlling time is prolonged, it exerts influence also upon releasing amount of the drug when transferred into the digestive tract so that sufficient drug release cannot be obtained.

In addition, JP-A-2000-327561 (the term "JP-A" as used herein means an published Japanese patent application) discloses an invention regarding a granulating composition which is characterized in that a physiologically active component is dispersed in a gelatin gel. Particularly, its "Detailed Description of the Invention" describes that, when a physiologically active component having an unpleasant taste is dispersed as a powder form in an aqueous solution in which gelatin is dissolved and then the gelatin solution is gelled, e.g., by spraying and cooling the dispersion, powder form of the component is dispersed in the gelatin gel so that it renders possible production of a granulating composition in the form of granules in which the unpleasant taste (e.g., bitterness, sourness or astringency) of the component having unpleasant taste is effectively masked.

In general, an advantage of the use of gelatin as a coating base or matrix base in a pharmaceutical preparation is that the thus obtained preparation is quickly dissolved after its administration, but sufficient drug release control cannot be obtained in most cases due to the high solubility of gelatin. In fact, as is evident from the test data of Table 1 of the specification, drug release control by the technique is limited to 3 to 5 minutes, further drug release control in the mouth cannot be expected from the technical idea that gelatin is used and a granulating composition is produced by dispersing a bitter drug in its gel. Particularly, when application to a drug having considerably low threshold value and application to a dosage form such as intrabuccally quick disintegrating tablets in which a drug is retained in the mouth are taken into consideration, it is considered that a release control of 5 to 10 minutes is necessary so that there is room for further improvement.

Accordingly, the object of the present invention is to provide a bitterness-reduced oral pharmaceutical composition which has excellent drug release-controlling ability in the mouth even 5 to 10 minutes after its administration and excellent drug release ability in the digestive tract and can be applied to intrabuccally quick disintegrating tablets without using capsules.

DISCLOSURE OF THE INVENTION

In the case of coating which uses, e.g., a polymer base, a method in which coating is carried out by preparing a coating solution by dissolving all components is generally used, and control of the desired drug release is achieved by the coating amount and ratio of the components. For example, it is possible to delay or quicken the release by mixing a water-insoluble polymer base with a water-soluble polymer base and changing their ratio, or to delay or quicken the release by changing the coating amount. However, when drug release is controlled to control bitterness in the mouth, it exerts influence upon releasing amount of the drug when transferred into the digestive tract so that sufficient drug release cannot be obtained.

Under such circumstances, the present inventors have hit upon an idea on a use mode for effectively bringing out characteristics of protein as means for solving the problems. That is, when various examinations were conducted based on our test results that a protein under water-insoluble state effected, e.g., by thermal denaturation dissolves at markedly high speed in a digestive tract-imitated test, it was found a possibility that a protein which slowly dissolves or does not dissolve in a buccal-imitated test solution dissolves during a markedly short period of time by the action of enzymes when it is transferred into the digestive tract-imitated test solution. Illustratively, it was found that when a solid protein is allowed to be present in a polymer base membrane as one of bitterness controlling components, namely when the protein is coated by dispersing it in a water or organic solvent solution of a polymer base, control of drug release in a buccal-imitated test solution and quick drug release in a digestive tract-imitated test solution are simultaneously achieved.

In general, when drug is controlled in a buccal-imitated test solution, reactivity in a digestive tract-imitated test solution is also reduced accompanied thereby, but drug control in the buccal-imitated test solution became possible by allowing a protein to be present in a polymer base membrane and quick drug release in the digestive tract-imitated test solution was achieved.

Detailed mechanism of such a phenomenon is still unclear but considered as follows.

I. Control of Drug Release in a Buccal-Imitated Test Solution (1) The protein is present in a polymer base membrane, particularly as particles,
(2) the buccal-imitated test solution starts to permeate into the polymer base membrane,
(3) since a certain period of time is required for the infiltration of protein in the polymer base membrane, formation of a channel for the permeation of test solution is slow, and
(4) since the drug permeability becomes low as the whole polymer base membrane, drug release control for 5 to 10 minutes after administration is achieved.

II. Quick Drug Release in a Digestive Tract-Imitated Test Solution (1) The digestive tract-imitated test solution starts to permeate into the polymer base membrane,
(2) the protein in the polymer base membrane undergoes actions of gastric or intestinal digestive enzymes in the digestive tract-imitated test solution and thereby expresses high solubility in the test solution, and
(3) since the drug permeability becomes high as the whole polymer base membrane by partial digestion of the protein, quick drug release is achieved.

In this connection, the term "buccal-imitated test solution" as used herein means phosphate buffer of pH 6.8 (The Pharmacopoeia of Japan, Disintegration Test second fluid; the same shall apply hereinafter), based on the knowledge that pH in the mouth is about 6.8, and the term "digestive tract-imitated test solution" as used herein means a buffer prepared by dissolving pepsin (Sigma) in hydrochloric acid buffer of pH 1.2 (The Pharmacopoeia of Japan, Disintegration Test First Fluid; the same shall apply hereinafter) when inside the stomach is simulated, or a buffer prepared by dissolving pancreatin (Sigma) in the phosphate buffer of pH 6.8 when inside the intestine is simulated.

In the same manner, the term "drug release in the mouth" means a result of dissolution test (The Pharmacopoeia of Japan, Dissolution Test Second Fluid) carried out using the buccal-imitated test solution, the term "excellent in the control of drug release in the mouth" means that, when the dissolution test (The Pharmacopoeia of Japan, Dissolution Test Second Fluid) is carried out using the buccal-imitated test solution, drug release ratio 10 minutes after commencement of the test (ratio of the amount of released drug at the time to the amount of the drug contained, unit is %) is from 0 to about 20%, and the term "excellent in the drug release ability in the digestive tract" means that, when the dissolution test is carried out using the digestive tract-imitated test solution, drug release ratio 45 minutes after commencement of the test is approximately from 70 to 100%.

The present invention, accomplished based on the above findings, relates to, 1. an oral pharmaceutical composition, which comprises one or more drugs having a bitter taste, one or more solid proteins and one or more pharmaceutically acceptable water-insoluble polymer bases, wherein the proteins are present in the polymer as particles,
2. the oral pharmaceutical composition according to the item 1, wherein the protein is one or more proteins selected from a bean protein or a processed bean protein product, a milk protein or a processed milk protein product, an egg protein or a processed egg protein product and gelatin,
3. the oral pharmaceutical composition according to the item 2, wherein the protein is a thermally denatured product,
4. the oral pharmaceutical composition according to the item 2, wherein the drug content is from 0.5 to 85% by weight based on the whole pharmaceutical preparation, the solid protein content is from 0.2 to 50% by weight based on the whole preparation and the water-insoluble polymer base content is from 0.2 to 50% by weight,
5. the oral pharmaceutical composition according to the item 4, wherein the pharmaceutically acceptable water-insoluble polymer base is pH-independent,
6. an intrabuccally quick disintegrating tablet, which comprises the oral pharmaceutical composition described in the item 5,
7. an intrabuccally quick disintegrating tablet, which comprises the oral pharmaceutical composition described in the item 5 and saccharides,
8. the intrabuccally quick disintegrating tablet according to the item 7, wherein the saccharides are granulated product prepared by using saccharides having low moldability spraying saccharides having high moldability as a binder, thereby effecting at least one of coating and granulating,
9. the intrabuccally quick disintegrating tablet according to the item 8, wherein the production process contains humidification and drying steps,
10. the intrabuccally quick disintegrating tablet according to the item 9, wherein the saccharides having low moldability are one or more saccharides selected from lactose, mannitol, glucose, sucrose, xylitol and erythritol,
11. the intrabuccally quick disintegrating tablet according to the item 9, wherein the saccharides having high moldability are one or more saccharides selected from maltose, maltitol, sorbitol and trehalose,
12. the oral pharmaceutical preparation, wherein it is prepared by coating core granules containing one or more drugs having a bitter taste with a coating solution containing one or more solid proteins or thermally denatured products thereof and one or more pharmaceutically acceptable water-insoluble polymer bases, and subsequently drying the granules,
13. the oral pharmaceutical composition according to the item 12, wherein the protein is one or more proteins selected from a bean protein or a processed bean protein product, a milk protein or a processed milk protein product, an egg protein or a processed egg protein product and gelatin, 14. the oral pharmaceutical composition according to the item 13, wherein the protein is a thermally denatured product,
15. the oral pharmaceutical composition according to the item 12, wherein the pharmaceutically acceptable water-insoluble polymer base is pH-independent,
16. an intrabuccally quick disintegrating tablet, which comprises the oral pharmaceutical composition described in the item 15,
17. an intrabuccally quick disintegrating tablet, which comprises the oral pharmaceutical composition described in the item 16 and saccharides,
18. the intrabuccally quick disintegrating tablet according to the item 17, wherein the saccharides are granulated product prepared by using saccharides having low moldability spraying saccharides having high moldability as a binder, thereby effecting at least one of coating and granulating,
19. the intrabuccally quick disintegrating tablet according to the item 18, wherein the production process contains humidification and drying steps,
20. the intrabuccally quick disintegrating tablet according to the item 19, wherein the saccharides having low moldability are one or more saccharides selected from lactose, mannitol, glucose, sucrose, xylitol and erythritol, and
21. the intrabuccally quick disintegrating tablet according to the item 19, wherein the saccharides having high moldability are one or more saccharides selected from maltose, maltitol, sorbitol and trehalose.

Other objects and advantages of the invention will become evident as the description progresses.

The bitterness-reduced oral pharmaceutical composition of the present invention is described further in detail.

The "solid protein" to be used in the present invention is not particularly limited with the proviso that it is a solid protein which is pharmaceutically acceptable and can attain the object of the invention by employing the constitution of the present invention, and its illustrative examples include bean proteins or processed products thereof, such as soybean protein or a processed soybean protein product and pea protein or a processed pea protein product, milk proteins or processed products thereof, such as casein, casein sodium, processed milk protein products and lactalbumin, egg proteins or processed products thereof, such as egg albumin, and gelatin, of which soybean protein, a processed soybean protein product and gelatin is preferred. These can be easily obtained as commercial products such as CP-GGG (Nitta Gelatin), Ajipron S3 (Ajinomoto), Ajipron SP1 (Ajinomoto) and Q-Lacto No. 5 (Q.P.).

The term "the protein is present as particles" as used herein means a condition that the protein is observed as particles in appearance when cross section of a film is observed using an electron microscope (SEM). The particle size which can be observed actually as particles cannot be defined clearly, but it is roughly from 500 nm to 100 $\mu$m when deduced from a result of SEM observation. In this connection, the particle size shown herein does not always coincide with the range of preferred particle size of the proteins shown in the embodiment of the present invention.

In order to facilitate the handling to include these proteins in a polymer base, it is desirable to use proteins in the form of powder.

When particle size distribution of the protein is not uniform or when small particles are desirable from the viewpoint of coating operation, it is possible to refine to a desired particle size using a pulverization apparatus such as jet mill pulverizer or sample mill pulverizer. Alternatively, it is possible to make particle sizes uniform by dispersing or dissolving the protein in an appropriate solvent (preferably water) and treating it by a known spray drying method, preferably by spray drying with a spray dryer. Particle size of the protein to be used in the present invention is not particularly limited but smaller particles are desirable in order to facilitate insurance of the drug release controlling ability in the buccal-imitated test solution the drug releasing ability in the digestive organ-imitated test solution.

Illustratively, it is from 1 to 50 $\mu$m, preferably from 1 to 30 $\mu$m, more preferably from 1 to 10 $\mu$m. The description as 1 $\mu$m is about the minimum value of particle size actually obtained by tests but is not a substantial lower limit value, because there is a possibility that the same effect of the present invention is confirmed when more smaller particle size is obtained, e.g., by a novel spray dryer.

In addition, the protein can be subjected to the present invention by treating it with heat. The heat treatment means a technique to denature the protein carried out using an apparatus such as an oven or a dryer, and its conditions can be optionally changed depending on each protein. Illustratively, a treating temperature of from 60 to 170° C., preferably from 90 to 160° C., more preferably from 100 to 140° C., can be employed. The treating time can also be optionally changed, and it is from 1 to 15 hours, preferably from 3 to 12 hours. Since the denaturation of protein intends to effect irreversible condensation accompanied by dehydration, longer time and higher temperature tend to decrease solubility of the protein or permeability of a drug and to reduce its solubility in the digestive tract-imitated test solution. Also, this step is not essential and can be optionally selected by examining releasing ability of the drug.

The "solid protein" can be used alone or by mixing two or more of them. Mixing amount of the protein varies depending, e.g., on the size of preparation particles so that cannot absolutely be defined, but is from 0.2 to 50% by weight, preferably from 1 to 40% by weight, more preferably from 5 to 30% by weight, based on the whole preparation. Excellent drug release ability in the digestive tract-imitated test solution cannot be obtained when the mixing amount is smaller than 0.2% by weight, and the period of time required for the production is prolonged when it is larger than 50% by weight.

The polymer base to be used in the present invention is not particularly limited with the proviso that it is pharmaceutically acceptable and can achieve the object of the present invention, and is a water-insoluble polymer base, and its illustrative examples include pH-independent polymer bases such as hydroxypropylmethylcellulose, ethyl cellulose and aminoalkylmethane acrylate copolymers RS and RL and pH-dependent polymer bases such as hydroxypropylmethyl acetate succinate, carboxymethylethylcellulose, an aminoalkyl methacrylate copolymer E and a methacrylic acid copolymer S. More preferred are water-insoluble and pH-independent polymer bases such as an aminoacryl methacrylate copolymer RS (trade name Eudlagit RS), ethyl cellulose and aminoalkyl methacrylate copolymer E, of which ethyl cellulose is most preferred. In addition, the polymer bases can also be used alone or by optionally combining two or more of them.

Mixing amount of the polymer base varies depending, e.g., on the size of preparation particles so that cannot absolutely be defined, but is from 0.2 to 50% by weight, preferably from 1 to 40% by weight, based on the whole preparation. Excellent drug control ability in the buccal-imitated test solution will be spoiled when the mixing amount is smaller than 0.2% by weight, and the production time will be prolonged when it is larger than 50% by weight.

The drug to be used in the present invention is not particularly limited with the proviso that it is used as a medically active component and has a bitter taste. Examples of the medically active component include central nervous system drugs such as a hypnotic sedative, a sleep inductor, an anxiolytic drug, an antiepileptic, an antipyretic-analgesic-anti-inflammatory drug, an antidepressant, an antiparkinsonism drug and a psychoneurosis drug, circulatory drugs such as a skeletal muscle relaxant, an autonomic drug, an antispasmodic agent, a cardiotonic agent, an arrhythmia drug, a diuretic agent, an antihypertensive drug, a vasoconstrictor, a coronary vasodilator, a peripheral vasodilator and a hyperlipemia drug, allergy drugs such as an antitussive expectorant and a bronchodilator, digestive organ drugs such as an antidiarrheal drug, a drug for controlling intestinal function, an antiulcer drug, a stomatic digestive drug and an antacid agent and hormone drugs such as a pituitary hormone drug, a thyroid hormone drug and an anti-thyroid hormone drug, as well as a urogenital organ drug, a vitamin compound, a hemostatic drug, a blood coagulation inhibitor, a pulmonary disease drug, an antidote, a habitual intoxication drug, a gout treating drug, a diabetic drug, an anti-malignant tumor drug, an antihistaminic drug, a crude drug, a Chinese orthodox medicine, an antibiotic, a chemotherapy drug, an anthelmintic drug and an anti-protozoan drug. Illustratively, meclofenoxate hydrochloride, chloramphenicol, aminophylline, erythromycin, josamycin, calcium hopantenate, phenobarbital, cimetidine, famotidine, etilefrine hydrochloride, diltiazem hydrochloride, propranolol hydrochloride, flufenamic acid, atolvastatin calcium, digitoxin, theophylline, promethazine hydrochloride, quinine hydrochloride, sulpyrine and ibuprofen can be exemplified. In addition, the drug can also be used alone or by optionally combining two or more of them.

Mixing amount of the drug is optionally selected generally in response to the kind of drugs or medical use (indication), though not particularly limited with the proviso that it is a therapeutically effective amount or a prophylactically effective amount. Mixing amount of the drug is preferably from 0.5% to 85% by weight, more preferably from 0.5% to 80% by weight, based on the whole pharmaceutical preparation. More preferred mixing amount of the drug is from 0.5% to 50% by weight, and most preferred mixing amount is from 0.5 to 10% by weight.

When the composition of the present invention is made into a pharmaceutical preparation, its dosage form is not particularly limited and various dosage forms generally used as medicaments can be selected. The composition of the present invention can be applied to any bitter drug and exerts particularly useful effects on a drug having a difficulty in preparing a medicament due to its bitterness, particularly on a drug having a markedly low threshold value. For example, it is a preferred embodiment to make the composition of the present invention into oral solid preparations such as granules, or dry syrups, capsules, tablets, troches or chewable tablets in which the granules are contained by a known method. In obtaining the pharmaceutical preparations, known methods generally used in this field can be used optionally, and one and/or two or more of conventionally used additives can be used by optionally combining them. Examples of such additives include binders, disintegrating agents, thickeners, fillers, lubricants, correctives and aromatics.

Also, the composition of the invention is a composition suitable for making intrabuccally quick disintegrating tablets by mixing it with an intrabuccally quick disintegrating tablet base and making the mixture into tablets. Examples of such intrabuccally quick disintegrating tablets include those which are described, e.g., in International Publication 95-20380, JP-A-8-19589 (corresponds to U.S. Pat. No. 5,672,364), JP-A-9-48726, Japanese Patent No. 2,919,771 and Japanese Patent No. 3,069,458 (corresponds to U.S. Pat. No. 5,720,974). Also, it is possible to make the composition of the invention into intrabuccally quick disintegrating tablets by granulating it using, e.g., the intrabuccally quick disintegrating tablet base and making the granules into tablets.

Illustratively, a step can be employed in which the composition of the invention is mixed with saccharides and the mixture is molded, preferably a step in which a granulated product is prepared by using saccharides having low moldability spraying saccharides having high moldability as a binder, thereby effecting coating and/or granulating, and the compound of the present invention is mixed with the granulated product and molded. The granulated product can also be molded by mixing the composition of the present invention with the saccharides having low moldability, and using the mixture spraying saccharides having high moldability as a binder, thereby effecting coating and/or granulating.

The term "saccharides having low moldability" as used herein means, e.g., that when 150 mg of saccharides are made into tablets using a punch of 8 mm in diameter under a tablet making pressure of from 10 to 50 kg/cm$^2$, the tablets show a hardness of from 0 to 2 kp, and the term "saccharides having high moldability" means that the hardness by the same method shows 2 kp or more. The saccharides having low moldability are those which are pharmaceutically acceptable, and their examples include lactose, mannitol, glucose, sucrose, xylitol and erythritol. It is possible to use them alone or by optionally combining two or more of them. The saccharides having high moldability are those which are pharmaceutically acceptable, and their examples include maltose, maltitol, sorbitol and trehalose. It is possible also to use these saccharides alone or by optionally combining two or more of them.

In addition, in order to improve hardness of the thus prepared moldings, humidification and drying steps can be employed. The "humidification" is determined by apparent critical relative humidity of the saccharides to be contained, but they are humidified generally to the critical relative humidity or more. For example, it is from 30 to 100 RH %, preferably from 50 to 90 RH %, as humidity. In this case, the temperature is preferably from 15 to 50° C., more preferably from 20 to 40° C. The treating time is from 1 to 36 hours, preferably from 12 to 24 hours. The "drying" is not particularly limited with the proviso that it is a step to remove moisture absorbed by the humidification For example, a drying temperature condition of from 10 to 100° C., preferably from 20 to 60° C., more preferably from 25 to 40° C., can be set. The treating time can be set to a period of from 0.5 to 5 hours, preferably from 1 to 3 hours.

Next, production method of the oral pharmaceutical composition of the present invention is described.

In order to produce the composition of the present invention, it is possible to use one or more bitter drugs itself as the core, but generally, granules which become the core (to be referred to as core granules hereinafter) containing a bitter drug are produced in advance. Known techniques can be applied to the production of core granules; for example, a bitter drug is mixed with an appropriate filler (e.g., microcrystalline cellulose, lactose or corn starch), and the mixture is made into granules, whole-grained and then dried, or the core granules are prepared by spraying a liquid prepared by dissolving or dispersing a bitter drug in a binder solution to appropriate particles (e.g., microcrystalline cellulose granules or sucrose granules) which become the core.

The step in which a coating solution containing the protein and polymer base is coated on the thus prepared granules comprises a step for preparing the coating solution and a step for actually carrying out the coating. The coating solution is prepared by dispersing the protein in a solution (e.g., water, ethanol or methanol) in which the polymer base is dissolved, and when masses are present, by filtering them using a screen (e.g., 60 mesh, sieve opening 250 µm). Regarding the protein, a step to make particle sizes uniform prior to the preparation of coating solution, if necessary after dissolving it in water and subsequent spray drying, or a step to denature it by heat treatment, can be optionally selected. The coating can be carried out using known apparatus and method, such as a fluidized bed granulating machine, and a desired composition is obtained by optionally adjusting the amount of the protein-containing coating solution for the granules containing a bitter drug.

In producing intrabuccally quick disintegrating tablets by mixing the composition of the present invention with an intrabuccally quick disintegrating tablet base, the intrabuccally quick disintegrating tablets can be obtained by employing the composition of the present invention as the drug of known intrabuccally quick disintegrating tablets described in the patents described above, using the intrabuccally quick disintegrating tablet bases described in the patents and in accordance with the methods described in the patents described above.

Illustratively, e.g., when the intrabuccally quick disintegrating tablets described in International Publication No. 95-20380 (corresponds to U.S. Pat. No. 5,576,014) are produced, the composition of the present invention is mixed with mannitol and then made into granules using a maltose aqueous solution. After making this granulated product into tablets, humidification and drying treatments are carried out as occasion demands, thereby obtaining the intrabuccally quick disintegrating tablets.

The present invention is based on a novel technical idea that a solid protein, particularly a bean protein or a processed bean protein product, a milk protein or a processed milk protein product or an egg protein or a processed egg protein product, is contained as granules in a polymer base, and is useful in that drug release control in the mouth and excellent drug release in the digestive tract were achieved at the same time by making granules containing a drug having a bitter taste into a composition by coating them by the technique so that it was able to provide an excellent bitterness-reduced oral pharmaceutical composition.

Accordingly, when the technique of the invention is applied to a drug having extremely low threshold value, it is possible to avoid reduction of drug release ratio in the digestive tract caused by a large amount of coating, which is found by the general coating techniques.

BEST MODE FOR CARRYING OUT THE INVENTION

The following illustratively describes the present invention with reference to examples, but the scope of the present invention is not restricted thereby.

EXAMPLE 1

[Preparation of Core Granules]

A 450 g portion of spherical granules of purified sucrose (Nonpalel, Freund Sangyo) were weighed, and a mixed solution of 1,466 g of methanol and 977 g of dichloromethane in which 450 g of acetaminophen (a product adapted to The Pharmacopoeia of Japan, Yoshitomi Pharmaceutical) and 90 g of hydroxypropylmethylcellulose (TC5E, Shin-etsu Chemical) had been dissolved was sprayed to the granules using a fluidized bed granulating machine (GPCG-1, Glatt) at a setting temperature of 80° C. and a material temperature of 40° C., in a feeding amount of 8 g/ml and under a spraying air pressure of 2 kg/cm$^3$, thereby obtaining core granules.

[Preparation of Coating Solution]

A 100 g portion of a processed soybean product (a processed soybean product containing soybean protein as the main component, mixed with casein sodium derived from milk protein; Ajipron SP1, mfd. by Ajinomoto) was put into 4,000 g of purified water and thoroughly dispersed and dissolved. This solution was spray-dried using a spray dryer (DL-40, mfd. by Yamato) to obtain a spray-dried preparation of processed soybean product having a particle size of roughly from 2 to 10 µm. The thus obtained spray-dried preparation was heat-treated at 140° C. for 12 hours in an oven, and a 21 g portion of the heat-treated preparation was dispersed in 69 g of an ethyl cellulose methanol solution (prepared by dissolving 14 g of ethyl cellulose (CP-10, Dow Chemical) in 55 g of methanol) and then filtered using a screen (60 mesh, sieve opening 250 µm) to obtain a coating solution.

[Operation of Coating]

Using a fluidized bed granulating machine (FLO-1, Freund-Ohgawara), 350 g of the core granules were coated at a setting temperature of 60° C. and a material temperature of 35 to 40° C., in a feeding amount of 6 g/ml and under a spraying air pressure of 2 kg/cm$^3$, thereby obtaining a coated product. Coated amount calculated from the weight of coated product and the weight of solid components in the coated coating solution was about 5% based on the core granules.

TEST EXAMPLE 1

The coated product obtained in Example 1 was weighed such that its amount as acetaminophen became 50 mg, and a dissolution test was carried out using an automatic six container dissolution tester (Toyama Sangyo) in accordance with The Pharmacopoeia of Japan, Dissolution Test Method 2 and using test solutions shown below (Table 1). Test solutions: 500 ml of phosphate buffer, pH 6.8 (The Pharmacopoeia of Japan, Disintegration Test second fluid), 500 ml of a pepsin test solution (The Pharmacopoeia of Japan, Disintegration Test first fluid, in which 1.6 g of pepsin (P-7000, Sigma) was dissolved) and 500 ml of a pancreatin test solution (The Pharmacopoeia of Japan, Disintegration Test second fluid, in which 5 g of pancreatin (P-1500, Sigma) was dissolved).

TABLE 1

| | Results of dissolution test in various test solutions (%) | | |
|---|---|---|---|
| Time (min.) | pH 6.8 | Pepsin | Pancreatin |
| 0 | 0 | 0 | 0 |
| 5 | 3.2 | 4.5 | 4.7 |
| 10 | 7.2 | 10.6 | 10.1 |
| 15 | 11.6 | 18.0 | 18.1 |
| 30 | 20.5 | 48.3 | 48.9 |
| 60 | 51.4 | 97.9 | 100 |

Results and Discussion

Release in the test solution which imitated inside the mouth (phosphate buffer, pH 6.8 (The Pharmacopoeia of Japan, Disintegration Test second fluid) was 7.2% after 10 minutes, and when compared with this result, evidently quick release was observed in the digestive tract-imitated test solutions (pepsin and pancreatin). Also, 45 minute values calculated on the assumption that the releasing ratio between 30 minutes and 60 minutes is constant were 36.0% in the pH 6.8 test solution, 73.1% in the pepsin test solution and 74.5% in the pancreatin test solution. Thus, it was considered that the pharmaceutical preparation of the invention can achieve drug release control in the mouth and excellent drug release in the digestive tract at the same time.

EXAMPLE 2

Weight of the heat-treated preparation of processed soybean product in Example 1 was changed to 56 g and dispersed in 170 g of an ethyl cellulose methanol solution (prepared by dissolving 14 g of ethyl cellulose (CP-10, Dow Chemical) in 156 g of methanol) and then the suspension was filtered using a screen (60 mesh, sieve opening 250 μm) to obtain a coated product by the same procedure of Example 1. Coated amount calculated from the weight of coated product and the weight of solid components in the coated coating solution was about 10% based on the core granules.

TEST EXAMPLE 2

The coated product obtained in Example 2 was weighed such that its amount as acetaminophen became 50 mg, and a dissolution test was carried out using an automatic six container dissolution tester (Toyama Sangyo) in accordance with The Pharmacopoeia of Japan, Dissolution Test Method 2 and using test solutions shown below.

Test solutions: The dissolution test was carried out using 500 ml of phosphate buffer, pH 6.8 (The Pharmacopoeia of Japan, Disintegration Test second fluid) and 500 ml of a pepsin test solution (The Pharmacopoeia of Japan, Disintegration Test first fluid, in which 1.6 g of pepsin (P-7000, Sigma) was dissolved).

As a result of the test, drug release in the test solution which imitated inside the mouth was 17.2% after 10 minutes, and drug release after 45 minutes in the digestive tract-imitated test solution (pepsin test solution) was 93.6% (calculated by the same method of Test Example 1, on the assumption that the releasing ratio between 30 minutes and 60 minutes is constant). Thus, it was confirmed that the pharmaceutical preparation of Example 2 is also excellent in the drug release control in the buccal-imitated test solution and excellent in the drug release in the digestive tract-imitated test solution.

EXAMPLE 3

A 50 g portion of gelatin (type GGG, Nitta Gelatin) was dissolved in 2,450 g of purified water which was heated at 80° C., and the gelatin solution was spray-dried using a spray dryer (DL-40, mfd. by Yamato) to obtain a spray-dried gelatin preparation. The thus obtained spray-dried preparation was treated at 155° C. for 3 hours in an oven. A 21 g portion of the thus obtained heat-treated preparation of spray-dried gelatin was dispersed in 69 g of an ethyl cellulose methanol solution (prepared by dissolving 14 g of ethyl cellulose (CP-10, Dow Chemical) in 55 g of methanol), filtered using a screen (60 mesh, sieve opening 250 μm) and then sprayed on 350 g of the core granules using a fluidized bed granulating machine (FLO-1, Freund-Ohgawara), thereby obtaining a coated product. Coated amount calculated from the weight of coated product and the weight of solid components in the coated coating solution was about 5% based on the core granules.

TEST EXAMPLE 3

The coated product obtained in Example 3 was weighed such that its amount as acetaminophen became 50 mg, and a dissolution test was carried out using an automatic six container dissolution tester (Toyama Sangyo) by the same method of Test Example 1.

As a result of the test, drug release in the test solution which imitated inside the mouth was 10.6% after 10 minutes, and drug release values after 45 minutes in the digestive tract-imitated pepsin test solution and pancreatin test solution were 79.0% and 79.1%, respectively. Thus, it was confirmed that the pharmaceutical preparation of Example 3 is also excellent in the drug release control in the buccal-imitated test solution and excellent in the drug release in the digestive tract-imitated test solution.

EXAMPLE 4

Using a fluidized bed granulating machine (UNI-GLATT, mfd. by Ogawara Kakoki), granules were obtained by granulating 380 g of mannitol (Towa Kasei Kogyo) with an aqueous solution containing 20 g of maltose (SunMalto S, Hayashibara).

A 384.5 mg portion of the granules were mixed with 115.5 mg (50 mg as acetaminophen) of the coated product produced in Example 1, packed in a punch of 11 mm in diameter and then made into tablets using an autograph (AGS-20kNG, mfd. by Shimadzu) under a tablet making pressure of 100 kg/cm to obtain intrabuccally quick disintegrating tablets.

While the present invention has been described in detail and with reference to specific embodiments thereof, it will be apparent to one skilled in the art that various changes and modifications can be made therein without departing from the scope thereof.

This application is based on Japanese patent application No. 2001-074190 filed Mar. 15, 2001, the entire contents thereof being hereby incorporated by reference.

What is claimed is:

1. An oral pharmaceutical composition, which comprises one or more drugs having a bitter taste, one or more solid proteins and one or more pharmaceutically acceptable water-insoluble polymer bases, wherein said solid proteins are present in a polymer base as particles and wherein the composition is prepared by coating said one or more drugs having a bitter taste with said polymer base having said proteins as particles dispersed therein.

2. The oral pharmaceutical composition according to claim 1, wherein the protein is one or more proteins selected from a bean protein or a processed bean protein product, a milk protein or a processed milk protein product, an egg protein or a processed egg protein product and gelatin.

3. The oral pharmaceutical composition according to claim 2, wherein the protein is a thermally denatured product.

4. The oral pharmaceutical composition according to claim 2, wherein the drug content is from 0.5 to 85% by weight based on the whole pharmaceutical preparation, the solid protein content is from 0.2 to 50% by weight based on the whole preparation and the water-insoluble polymer base content is from 0.2 to 50% by weight based on the whole preparation.

5. The oral pharmaceutical composition according to claim 4, wherein the pharmaceutically acceptable water-insoluble polymer base is pH-independent.

6. An intrabuccally quick disintegrating tablet, which comprises the oral pharmaceutical composition described in claim 5.

7. An intrabuccally quick disintegrating tablet, which comprises the oral pharmaceutical composition described in claim 5 and saccharides.

8. The intrabuccally quick disintegrating tablet according to claim 7, wherein the saccharides are a granulated product prepared by spraying saccharides having low moldability with saccharides having high moldability as a binder, thereby effecting at least one of coating and granulating.

9. The intrabuccally quick disintegrating tablet according to claim 8, wherein the production process contains humidification and drying steps.

10. The intrabuccally quick disintegrating tablet according to claim 9, wherein the saccharides having low moldability are one or more saccharides selected from lactose, mannitol, glucose, sucrose, xylitol and crythritol.

11. The intrabuccally quick disintegrating tablet according to claim 9, wherein the saccharides having high moldability are one or more saccharides selected from maltose, maltitol, sorbitol and trehalose.

12. The oral pharmaceutical composition according to claim 5, prepared by coating core granules of said one or more drugs having a bitter taste with said polymer base having said proteins as particles dispersed therein and subsequently drying the granules.

13. The oral pharmaceutical composition according to claim 12, wherein the protein is a thermally denatured product.

14. An intrabuccally quick disintegrating tablet, which comprises the oral pharmaceutical composition described in claim 12.

15. An intrabuccally quick disintegrating tablet, which comprises the oral pharmaceutical composition described in claim 14 and saccharides.

16. The intrabuccally quick disintegrating tablet according to claim 15, wherein the saccharides are a granulated product prepared by spraying saccharides having low moldability with saccharides having high moldability as a binder, thereby effecting at least one of coating and granulating.

17. The intrabuccally quick disintegrating tablet according to claim 16, wherein the production process contains humidification and drying steps.

18. The intrabuccally quick disintegrating tablet according to claim 17, wherein the saccharides having low moldability are one or more saccharides selected from lactose, mannitol, glucose, sucrose, xylitol and crythritol.

19. The intrabuccally quick disintegrating tablet according to claim 17, wherein the saccharides having high moldability arc one or more saccharides selected from maltose, maltitol, sorbitol and trehalose.

* * * * *